(12) United States Patent
Muhanna et al.

(10) Patent No.: US 7,815,680 B2
(45) Date of Patent: Oct. 19, 2010

(54) FLEXIBLE VERTEBRAL IMPLANT

(75) Inventors: Nabil L. Muhanna, 2128 Valley Rd., Gainesville, GA (US) 30501; David L. Schalliol, Oakwood, GA (US)

(73) Assignee: Nabil L. Muhanna, Gainesville, GA (US)

(*) Notice: Subject to any disclaimer, the term of this patent is extended or adjusted under 35 U.S.C. 154(b) by 312 days.

(21) Appl. No.: 11/331,005

(22) Filed: Jan. 13, 2006

(65) Prior Publication Data

US 2007/0168032 A1    Jul. 19, 2007

(51) Int. Cl.
*A61F 2/44* (2006.01)
(52) U.S. Cl. ................... 623/17.15; 623/17.11
(58) Field of Classification Search .... 623/17.11–17.16
See application file for complete search history.

(56) References Cited

U.S. PATENT DOCUMENTS

| | | | |
|---|---|---|---|
| 1,399,646 A * | 12/1921 | Oppman .................. 59/90 |
| 2,618,922 A * | 11/1952 | Johnson .................. 59/85 |
| 2,621,470 A * | 12/1952 | Robbins .................. 59/85 |
| 3,031,219 A * | 4/1962 | Robbins .................. 403/373 |
| 5,609,636 A | 3/1997 | Kohrs et al. |
| 5,616,144 A | 4/1997 | Yapp et al. |
| 5,776,196 A | 7/1998 | Matsuzaki et al. |
| 5,780,919 A | 7/1998 | Chua et al. |
| 5,865,848 A | 2/1999 | Baker |
| 5,895,428 A * | 4/1999 | Berry .................. 623/17.15 |
| 5,989,291 A | 11/1999 | Ralph et al. |
| 6,063,121 A * | 5/2000 | Xavier et al. .......... 623/17.15 |
| 6,520,996 B1 * | 2/2003 | Manasas et al. ........ 623/23.5 |
| 6,582,466 B1 * | 6/2003 | Gauchet ................ 623/17.11 |
| 6,673,113 B2 * | 1/2004 | Ralph et al. .......... 623/17.13 |
| 6,802,867 B2 * | 10/2004 | Manasas et al. ........ 623/23.5 |
| 6,824,565 B2 | 11/2004 | Muhanna et al. |
| 6,936,070 B1 | 8/2005 | Muhanna |
| 7,214,244 B2 * | 5/2007 | Zubok et al. .......... 623/17.14 |
| 7,229,441 B2 * | 6/2007 | Trieu et al. ............ 606/279 |
| 7,291,171 B2 * | 11/2007 | Ferree ................. 623/17.11 |
| 7,309,357 B2 * | 12/2007 | Kim .................... 623/17.13 |
| 7,314,486 B2 * | 1/2008 | Ralph et al. .......... 623/17.13 |
| 7,320,707 B2 * | 1/2008 | Zucherman et al. ..... 623/17.14 |
| 7,338,525 B2 * | 3/2008 | Ferree ................. 623/17.11 |
| 2002/0128714 A1 * | 9/2002 | Manasas et al. ........ 623/17.15 |
| 2004/0039448 A1 * | 2/2004 | Pisharodi ............. 623/17.15 |
| 2005/0102028 A1 * | 5/2005 | Arnin et al. .......... 623/17.13 |
| 2006/0136062 A1 * | 6/2006 | DiNello et al. ........ 623/17.14 |
| 2007/0073403 A1 * | 3/2007 | Lombardo et al. ...... 623/17.13 |

* cited by examiner

*Primary Examiner*—Eduardo C Robert
*Assistant Examiner*—Ellen C Hammond
(74) *Attorney, Agent, or Firm*—Womble Carlyle Sandridge & Rice, PLLC

(57) ABSTRACT

A vertebral implant for replacing a biological disk includes a top and bottom plate. The implant further includes flexible coupling that couples together the plates while allowing the same degree of freedom in all axes of motion as the original biological disk.

8 Claims, 10 Drawing Sheets

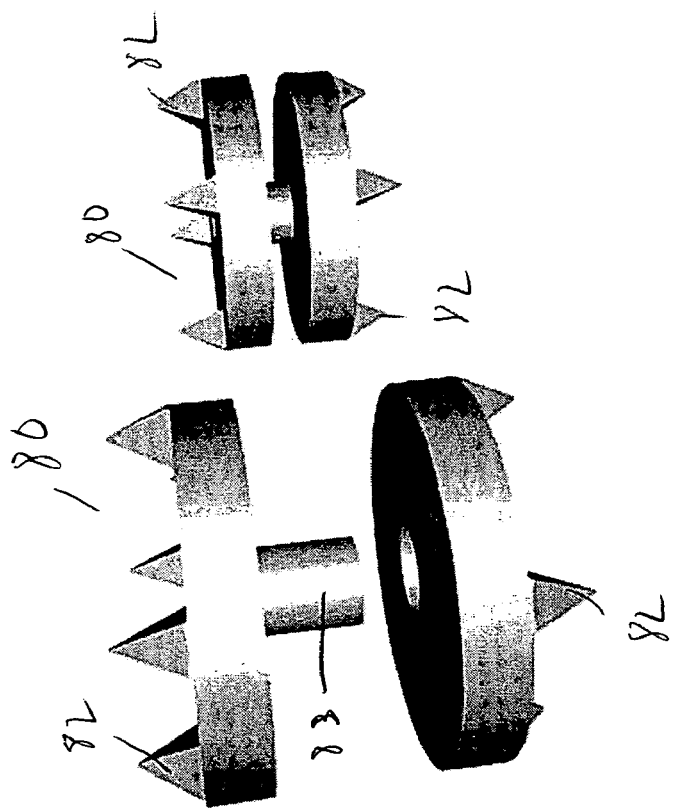

FLEXIBLE VERTEBRAL IMPLANT

FIELD OF THE INVENTION

One embodiment of the present invention is directed to a medical device. More particularly, one embodiment of the present invention is directed to a flexible vertebral implant for replacing an intervertebral disc.

BACKGROUND INFORMATION

The spinal column, which is the central support to the vertebrate skeleton and a protective enclosure for the spinal cord, is a linear series of bones, or vertebrae. Intervertebral discs separate and reduce friction between adjacent vertebrae and absorb compression forces applied to the spinal column. Spinal nerves that extend from each side of the spinal cord exit the column at intervertebral foramina.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human, are two superior articulated processes that oppose two inferior articulated processes extending from the lower surface of an adjacent vertebra. Facets on the opposing processes determine the range and direction of movement between adjacent vertebrae, and hence the flexibility of the spinal column.

The intervertebral discs include the fibrillar cartilage of the anulus fibrosus, a fibrous ring, the center of which is filled with an elastic fibrogelatinous pulp that acts as a shock absorber. The outer third of the anulus fibrosus is innervated. The entire spinal column is united and strengthened by encapsulating ligaments.

Back pain is one of the most significant problems facing the workforce in the United States today. It is a leading cause of sickness-related absenteeism and is the main cause of disability for people aged between 19 and 45. Published reports suggest that the economic cost is significant, treatment alone exceeding $80 billion annually. Although acute back pain is common and typically treated with analgesics, chronic pain may demand surgery for effective treatment.

Back pain can occur from pinching or irritation of spinal nerves, compression of the spine, vertebral shifting relative to the spinal cord axis, and bone spur formation. The most common cause of disabling back pain, however, stems from trauma to an intervertebral disc, resulting from mechanical shock, stress, tumors or degenerative disease, which may impair functioning of the disc and limit spinal mobility. In many cases, the disc is permanently damaged and the preferred treatment becomes partial or total excision.

Another cause of back injury is herniation of the intervertebral disc, wherein the gelatinous fluid of the nucleus pulposus enters the vertebral canal and pressures the spinal cord. Again, surgery is often the only method available for permanent relief from pain or the neurological damage ensuing from the pressure of fluid on the spinal cord, and requires replacement of the damaged disc.

Traumatic injury to an intervertebral disc that is not removed will frequently promote scar tissue formation. Scar tissue is weaker than original healthy tissue so that the disc will progressively degenerate, lose water content, stiffen and become less effective as a shock absorber. Eventually, the disc may deform, herniate, or collapse, limiting flexibility of the spinal column at that position. The only option is for the intervertebral disc to be partially or totally removed.

When the disc is partially or completely removed, it is necessary to replace the excised material to prevent direct contact between hard bony surfaces of adjacent vertebrae. One vertebral body replacement that may be inserted between adjacent vertebrae, according to U.S. Pat. No. 5,989,291 to Ralph et al., includes two opposing plates separated by a belleville washer or a modified belleville washer. The washer functions to provide a restorative force to mimic the natural functions of the disc of providing a shock absorber and mobility between adjacent vertebrae. However, mechanical devices intended to replicate intervertebral disc function have had only limited success. An alternative approach is a "cage" that maintains the space usually occupied by the disc to prevent the vertebrae from collapsing and impinging the nerve roots.

Spinal fusion may be used to restrict the motion, between two vertebrae, that comes from segmental instability. Fusing the vertebrae together, however, reduces the mechanical back pain by preventing the now immobile vertebrae from impinging on the spinal nerve. The disadvantage of such body replacements is that stability is created at the expense of the flexibility of the spine.

Surgical procedures for replacing intervertebral disc material, rather than fusing of the vertebrae, have included both anterior approaches and posterior approaches to the spinal column. The posterior approach (from the back of the patient) encounters the spinous process, superior articular process, and the inferior articular process that must be removed to allow insertion of the disc replacement material into the intervertebral space. The excess removal of the bony process triggers further degradation and impediment of the normal movement of the spine. The anterior approach to the spinal column is complicated by the internal organs that must be bypassed or circumvented to access the vertebrae.

Many intervertebral body replacements require preparation of the surfaces of the adjacent vertebrae to accommodate the body replacement, causing significant tissue and bone trauma. For example, chiseling or drilling of the vertebral surface may be required to prepare a receiving slot. They may also require screwing the body replacement into the intervertebral space, making installation difficult and increasing trauma to the vertebral tissue. Many body replacements include complex geometries and are costly to manufacture. Examples of such geometrically complex body replacements are described in U.S. Pat. No. 5,609,636 to Kohrs et al., U.S. Pat. No. 5,780,919 to Zdeblick et al., U.S. Pat. No. 5,865,848 to Baker and U.S. Pat. No. 5,776,196 to Matsuzaki et al. Many of these complex body replacements may require screwing the body replacement into the intervertebral space, thereby making installation difficult and traumatic to the vertebral tissue. Further, many of these replacements, like spinal fusion, limit the flexibility between the vertebrae.

Based on the foregoing, there is a need for an improved flexible vertabral implant.

SUMMARY OF THE INVENTION

One embodiment of the present invention is a vertebral implant for replacing a biological disk. The implant includes a top and bottom plate. The implant further includes flexible coupling that couples together the plates while allowing the same degree of freedom in all axes of motion as the original biological disk.

BRIEF DESCRIPTION OF THE DRAWINGS

FIG. 10 is two perspective views of a flexible vertebral implant in accordance with still another embodiment of the present invention.

DETAILED DESCRIPTION

One embodiment of the present invention is a vertebral implant that is flexible because it includes a joint that allows rotation, tilt, compression and tension.

Figure 1:
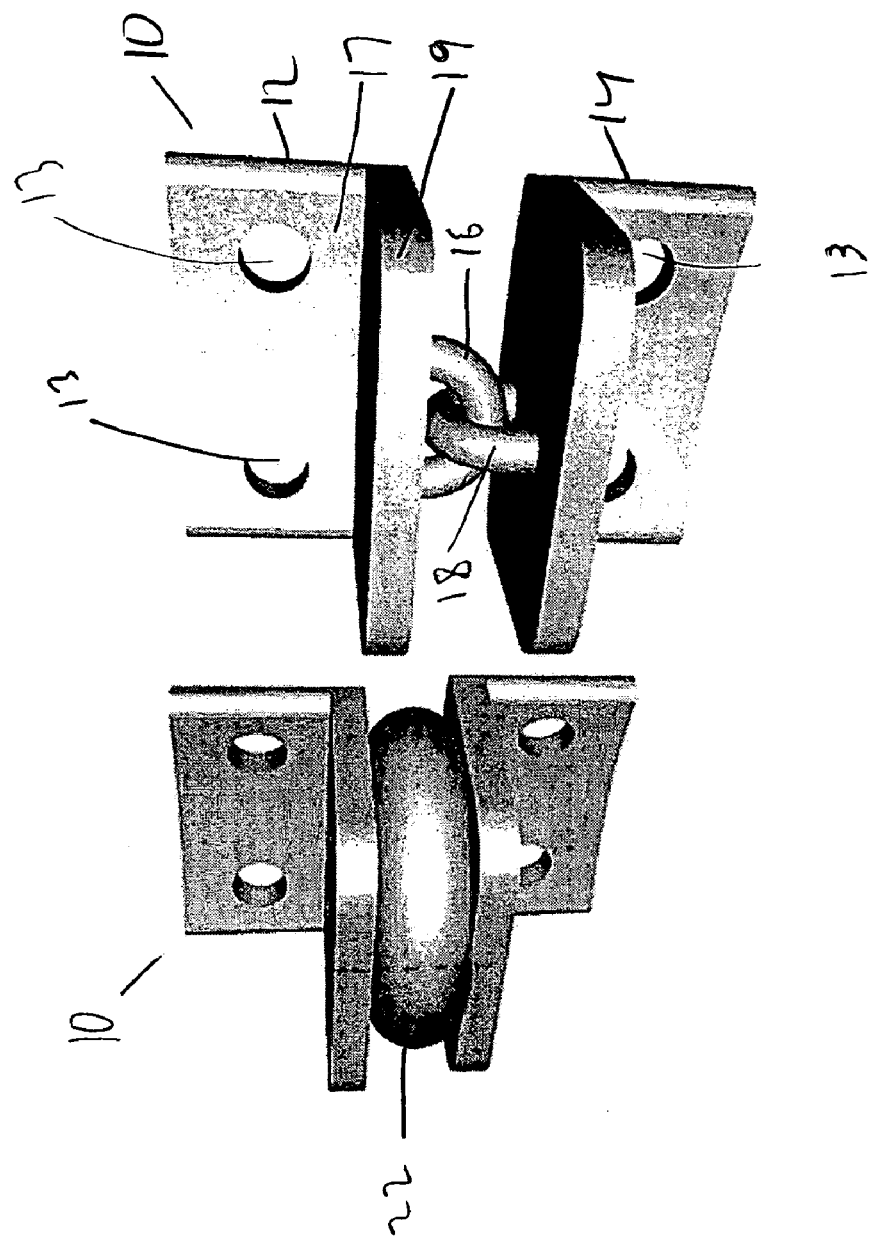
FIG. 1 is two perspective views of a flexible vertebral implant in accordance with one embodiment of the present invention.

FIG. 1 is two perspective views of a flexible vertebral implant 10 in accordance with one embodiment of the present invention. Flexible vertebral implant 10 includes two L-shaped plates 12 and 14, one of which is superior (top, plate 12) and one of which is inferior (bottom, plate 14). Plates 12 and 14 include a portion 19 adapted to be inserted between the vertebrae, and an angled bracket 17 adapted to be fixed to a vertebral body by screws through holes 13. The vertebral contact surfaces of angled bracket 17 in one embodiment are roughened and treated to stimulate bone growth, to assure fusion between the original bone and the metal surfaces. The mounting screws may be of the same type that is typically used to secure fixed cervical plates.

Each plate includes a link 16 and 18 which is adapted to hold the plates at a controlled distance from one another, and still allow rotation or angular motion. In the embodiment shown in FIG. 1, links 16 and 18 are chain links, but other types of links or posts can be used. Links 16 and 18 can be made of metal, or can be made of various biocompatable fibrous materials in the form of a cord or rope. When links 16, 18 are made from metal, a Teflon or other type of biocompatible material will be at least on the inside of the links to avoid metal to metal contact.

The right perspective view of FIG. 1 illustrates flexible vertebral implant 10 without a cushioning material in order to allow a view of links 16 and 18. The left perspective view of FIG. 1 illustrates flexible vertebral implant 10 with cushioning filler material 22 between plates 12 and 14 and surrounding links 16 and 18. Cushioning filler material 22 can be an inserted elastomeric O-ring of biocompatible material, an injected elastomeric cushion of biocompatible material, or a multi-layered cloth build up of biocompatible material.

As shown, the chain-link joint of links 16 and 18 has clearances that will allow rotation, tilt, compression, and tensile pull. Links 16, 18 may be factory welded to the L-shaped plates 12, 14 for maximum strength. All degrees of freedom are controlled by the mechanical clearances of this chain-link joint. The dampening and sealing of the joint is accomplished by the installation of an elastomeric O-ring (torroid), and then the injection of the internal cavity by a viscous elastomeric material that will then be cured or hardened to the desired cushion properties. The injection process provides an elastomeric pad or cushion between all metal parts, to make the joint quiet, sealed, and with the desired level of stiffness.

Figure 2:
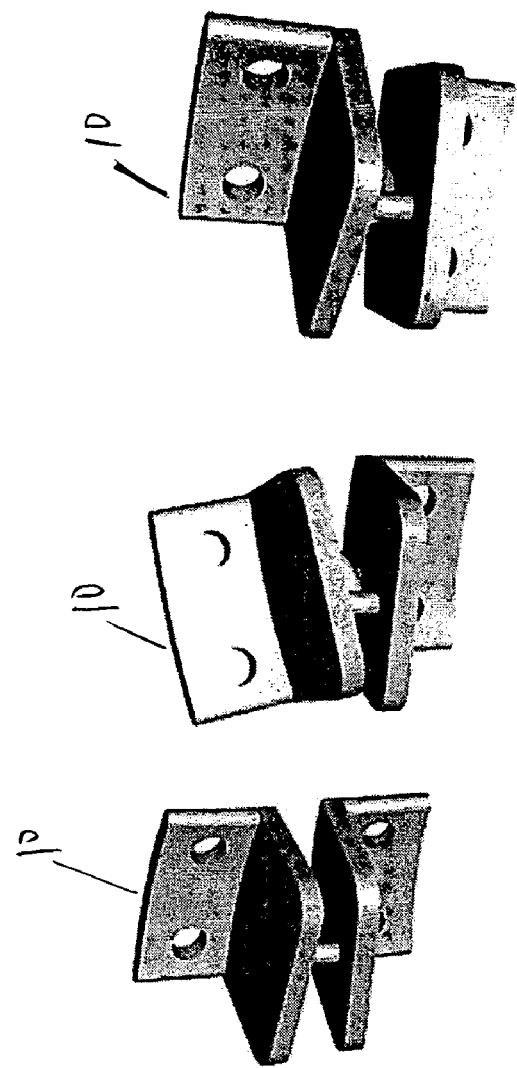
FIG. 2 illustrates three perspective views of the flexible vertebral implant of FIG. 1 without the presence of filler material in accordance with one embodiment of the present invention.

FIG. 2 illustrates three perspective views of flexible vertebral implant 10 of FIG. 1 without the presence of filler material 22. As shown, the mechanical joint allows flexibility in all axes. The degree of freedom is controlled by the metal to metal clearances between adjacent members. This freedom is also controlled and dampened by the elastomeric pads and fillers placed inside the cavity.

Figure 3:
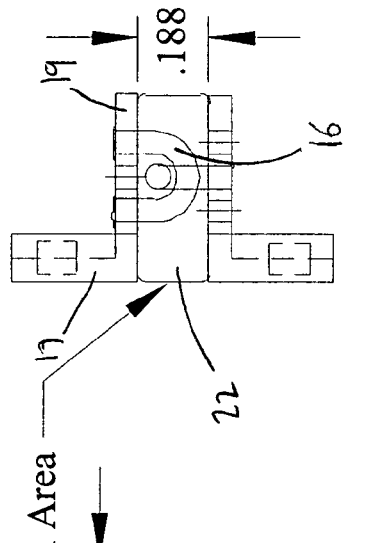
FIG. 3 is a plan diagram showing the relative sizing and detail of the components of the flexible vertebral implant in accordance with one embodiment of the present invention.
Figure 3:
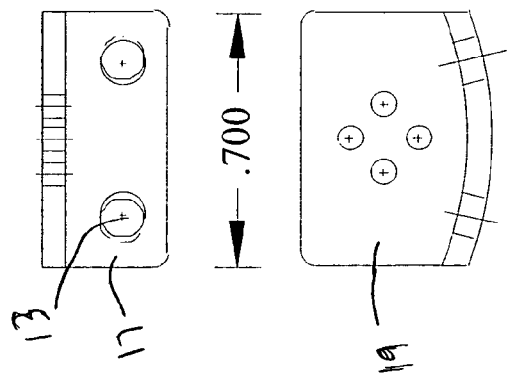

FIG. 3 is a plan diagram showing the relative sizing and detail of the components of flexible vertebral implant 10. In one embodiment, all metal material is formed from titanium.

Figure 4:
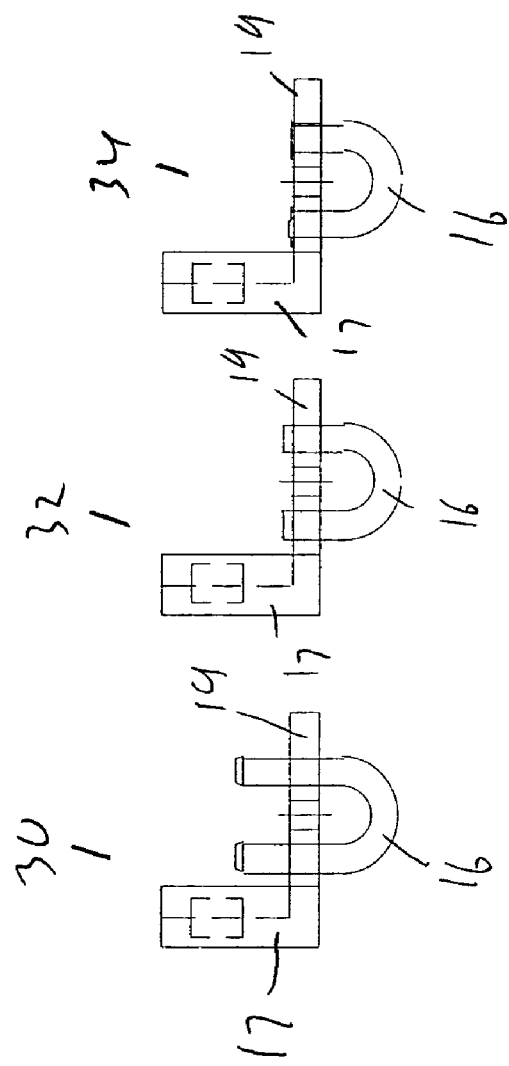
FIG. 4 is a sequential plan diagram showing a manufacturing method of the flexible vertebral implant in accordance with one embodiment of the present invention.

FIG. 4 is a sequential plan diagram showing a manufacturing method of flexible vertebral implant 10 in accordance with one embodiment of the present invention. At 30, link 16 is inserted through the holes of portion 19 of the plate. At 32 the excess metal portion of link 16 is removed. At 34 the link 16 is welded to portion 19 of the plate.

Figure 5:
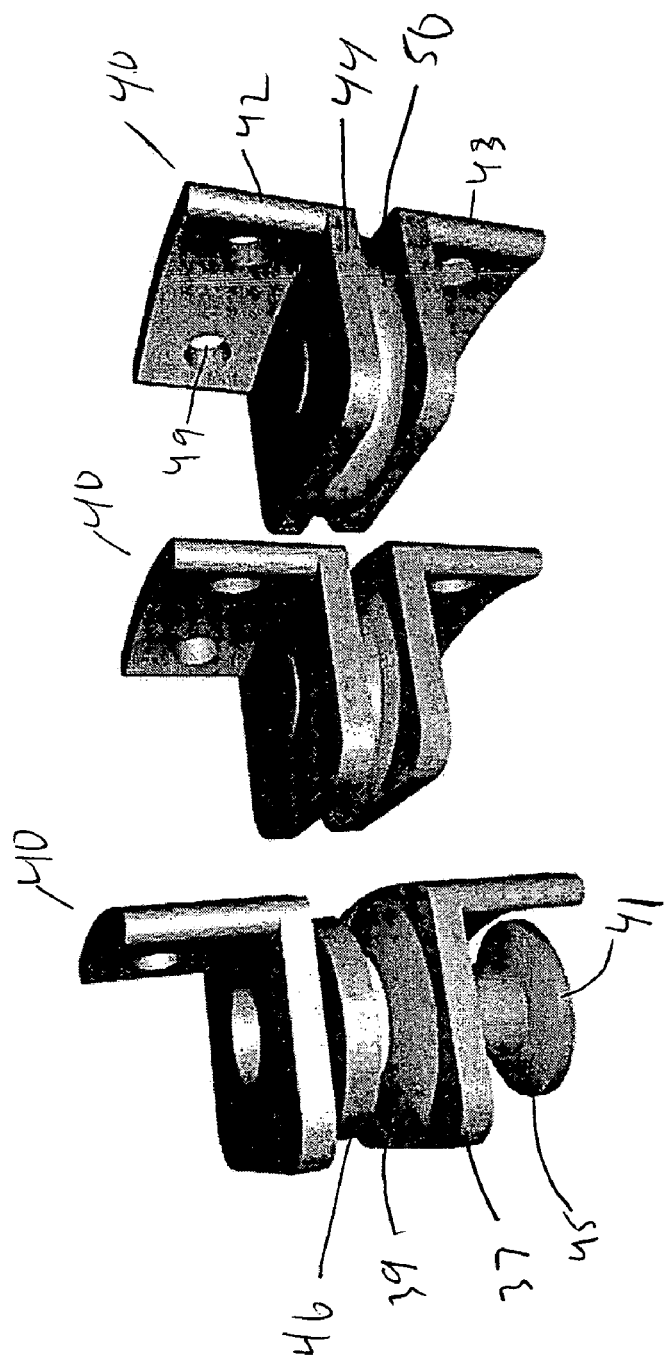
FIG. 5 is three perspective views of a flexible vertebral implant in accordance with another embodiment of the present invention.

FIG. 5 is three perspective views of a flexible vertebral implant 40 in accordance with another embodiment of the present invention. Flexible vertebral implant 40 includes two L-shaped plates 42 and 43, one of which is superior (top, plate 42) and one of which is inferior (bottom, plate 43). Plates 42 and 43 include a portion 44 and 37, respectively, adapted to be inserted between the vertebrae, and an angled bracket 42 adapted to be fixed to a vertebral body by screws through holes 19.

Unlike the chain link embodiments disclosed above, flexible vertebral implant 40 uses a welded stud 41 to couple plates 42 and 43 together. Bottom plate 43 includes a spherical hollow dome 39. Placed on top of dome 39 is conforming spherical collar 46, which may be made of Teflon or other biocompatable plastic material such as polyethylene. Collar 46 forms an aligning bearing between the plates. Metal stud 41 is placed through the assembly and welded into top plate 42. Metal stud 41 has a spherical surface 45 that mates with the bottom surface of domed bottom plate 43.

Flexible vertebral implant 40 further includes an elastomeric O-Ring 50, which provides sealing and dampening of motion. Mechanical clearances around the stud shank and the spherical head provide relative rotary and alignment motion between the plates.

Figure 6:
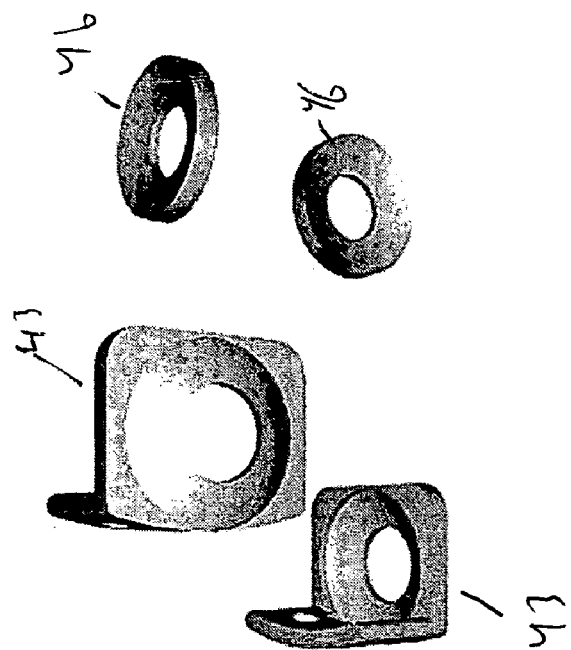
FIG. 6 illustrates multiple perspective views of a metal stud, a bottom plate, and collar.
Figure 6:
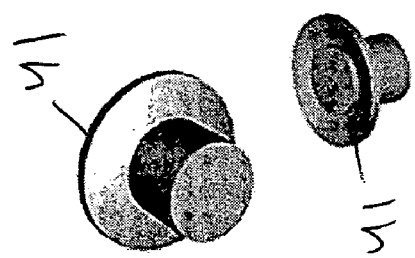

FIG. 6 illustrates multiple perspective views of metal stud 41, bottom plate 43, and collar 46.

Figure 7:
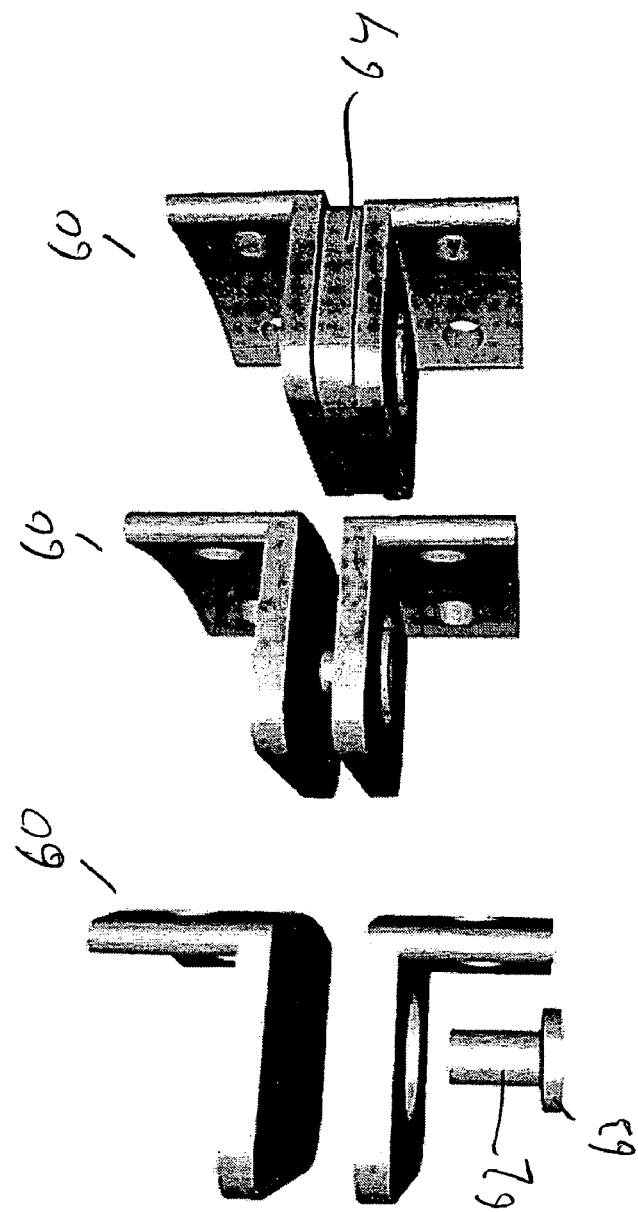
FIG. 7 is three perspective views of a flexible vertebral implant in accordance with still another embodiment of the present invention.

FIG. 7 is three perspective views of a flexible vertebral implant 60 in accordance with still another embodiment of the present invention. Implant 60 is similar to implant 40 of FIG. 5, but lacks the floating spherical collar between the plates. The plates are assembled with a bolt 62 that passes through the bottom plate and is welded to the top plate. The entire void between the plates is filled with a rubber like elastomer 64, which is molded or vulcanized to the plates. Bolt 62 serves primarily as a backup safety device in the event of a failure of the elastomeric bond to the plates. The head 63 of bolt 62 has radial clearance where it passes through the bottom plate, and has a small convex spherical bearing surface that matches a concave spherical bearing surface in the plate.

Figure 8:
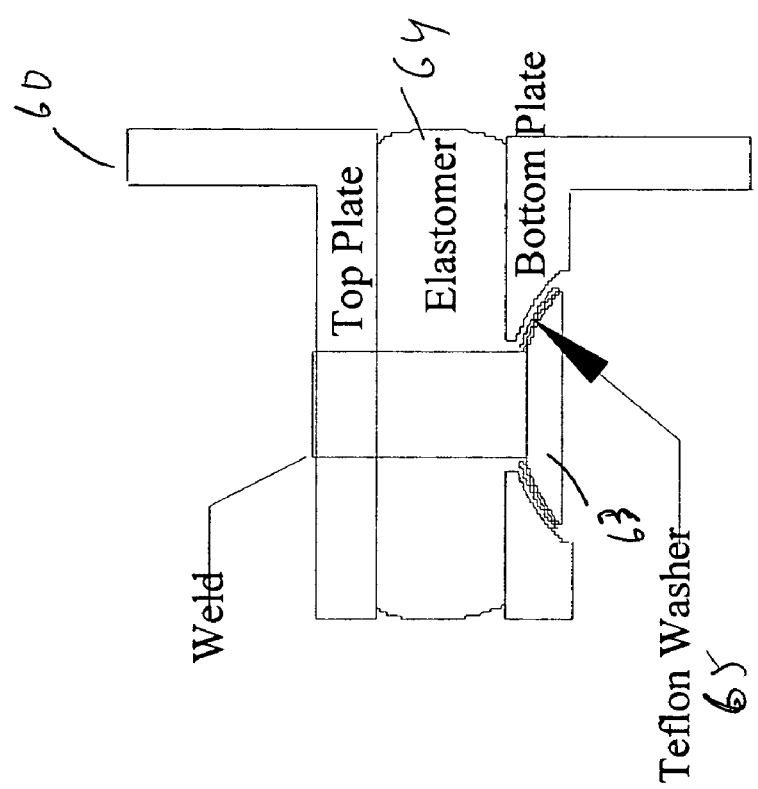
FIG. 8 is a side view of an implant in accordance with one embodiment of the present invention.

FIG. 8 is a side view of implant 60 in accordance with one embodiment of the present invention. As shown, a thin Teflon washer 65 is placed between bolt head 63 and the concave spherical bearing surface in the plate to prevent metal to metal contact. These clearances and bearing surfaces allow relative motion between the plates as the elastomer is flexed.

Figure 9:
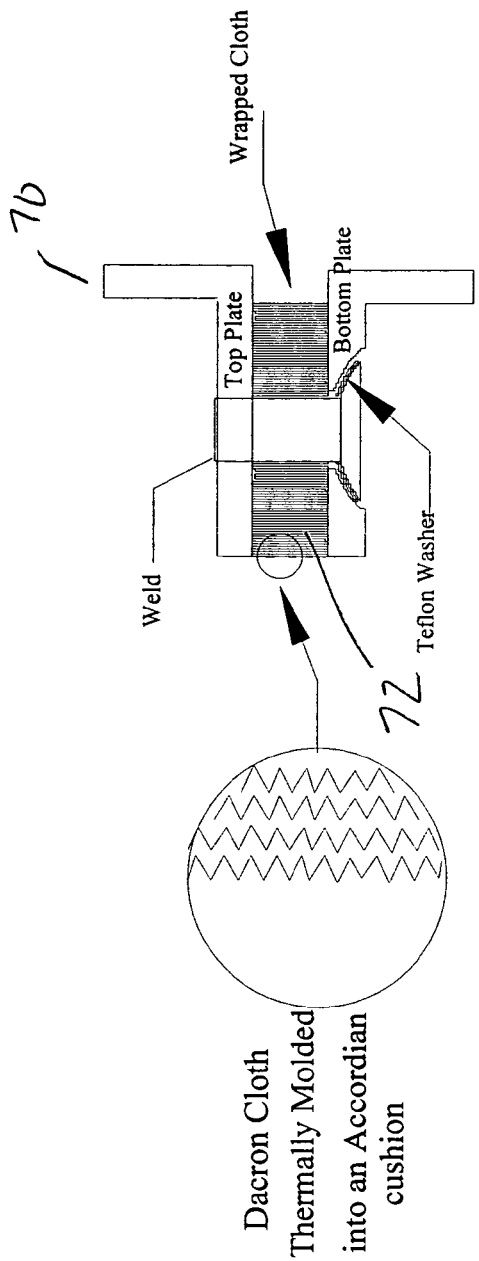
FIG. 9 is a side view of a flexible vertebral implant in accordance with still another embodiment of the present invention.

FIG. 9 is a side view of a flexible vertebral implant 70 in accordance with still another embodiment of the present invention. Implant 70 is identical to implant 60 shown in FIG. 8, except that it includes a biocompatible Dacron cloth 72 in place of elastomer 64. Cloth 72 is thermally molded into an accordion texture to improve its compressibility properties. A similar Dacron cloth with the accordion texture is currently being used in vascular surgery as artificial blood vessels. In one embodiment, cloth 72 is formed from strips or tape, and then wrapped around the center vertical connecting link or post.

FIG. 10 is two perspective views of a flexible vertebral implant 80 in accordance with still another embodiment of the present invention. Unlike the prior disclosed embodiments, implant 10 does not include the angle flanges. Instead, implant 80 includes pointed barbs 82 that embed into the end plate of the vertebral body. The center post or vertical link 83 shown in FIG. 10 is generic. It can be formed as disclosed in any of the flexible couplings in the previously disclosed embodiments, such as a chain-link, a bolt, a stud, or a cord (rope). Implant 80 further includes an elastomeric cushion (not shown) which will fill the void between the plates such as disclosed in the previous embodiments.

As disclosed, flexible vertebral implants of the present invention, unlike prior art implants, provide the same degree of freedom in all axes of motion as the original biological disc. They provide a cushioned joint for compression, tension, rotation, and tilt. The backlash or internal clearances between the metal parts are fully dampened by elastomeric pads, which provides a quiet, click free, low friction motion joint nearly identical to the original biological disc. The four degrees of motion freedom are fully controlled by the internal geometry of the joint. The stiffness of the joint is fully controllable by the selection of the biocompatable elastomeric or of cloth pad material.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A vertebral implant comprising:
   a first plate;
   a flexible coupling coupled to said first plate;
   a second plate coupled to said flexible coupling,
   wherein said flexible coupling comprises a first rigid link affixed to said first plate such that, when said first rigid link is affixed to said first plate, said first rigid link and said first plate form a unitary structure not affixed to said second plate and a second rigid link affixed to said second plate such that, when said second rigid link is affixed to said second plate, said second rigid link and said second plate form a unitary structure not affixed to said first plate;
   said first rigid link and said second rigid link being movably interconnected with each other; and
   wherein said first rigid link and said second rigid link define clearance within said flexible coupling such that ranges of motion of said flexible coupling include at least longitudinal, transverse, and combinations thereof and wherein said first link comprises a chain link and said second link comprises a chain link.

2. The vertebral implant of claim 1, further comprising a cushioning layer surrounding said flexible coupling.

3. The vertebral implant of claim 2, wherein said cushioning layer comprises an elastomeric O-ring.

4. The vertebral implant of claim 2, wherein said cushioning layer comprises an injected elastomeric cushion.

5. The vertebral implant of claim 2, wherein said cushioning layer comprises a multi-layer cloth.

6. The vertebral implant of claim 1, said first plate comprising an angled bracket adapted to be fixed to a vertebral body via mounting screws.

7. The vertebral implant of claim 1, wherein said ranges of motion further include rotation and tilt.

8. The vertebral implant of claim 1, wherein said first rigid link and said second rigid link are movably interconnected only with each other.

\* \* \* \* \*